(12) United States Patent
Zabrouskov et al.

(10) Patent No.: US 8,748,809 B2
(45) Date of Patent: Jun. 10, 2014

(54) ACQUISITION AND ANALYSIS OF MIXED ION POPULATIONS IN A MASS SPECTROMETER

(75) Inventors: Vladimir Zabrouskov, Belmont, CA (US); Michael W. Senko, Sunnyvale, CA (US); Scott T. Quarmby, Round Rock, TX (US)

(73) Assignee: Thermo Finnigan LLC, San Jose, CA (US)

( * ) Notice: Subject to any disclaimer, the term of this patent is extended or adjusted under 35 U.S.C. 154(b) by 425 days.

(21) Appl. No.: 13/265,127

(22) PCT Filed: Mar. 30, 2010

(86) PCT No.: PCT/US2010/029277
§ 371 (c)(1),
(2), (4) Date: Oct. 18, 2011

(87) PCT Pub. No.: WO2010/120496
PCT Pub. Date: Oct. 21, 2010

(65) Prior Publication Data
US 2012/0049056 A1 Mar. 1, 2012

Related U.S. Application Data

(60) Provisional application No. 61/168,714, filed on Apr. 13, 2009.

(51) Int. Cl.
*H01J 49/00* (2006.01)
*G01N 30/72* (2006.01)

(52) U.S. Cl.
CPC .......... *H01J 49/0031* (2013.01); *H01J 49/004* (2013.01); *G01N 30/7206* (2013.01); *G01N 30/7233* (2013.01)
USPC .......................................... 250/282; 250/281

(58) Field of Classification Search
CPC ............................... H01J 49/00; H01J 49/004
USPC ................................................ 250/281–300
See application file for complete search history.

(56) References Cited

U.S. PATENT DOCUMENTS

| 6,900,430 | B2 | 5/2005 | Okumura et al. |
| 7,049,583 | B2 | 5/2006 | Bateman et al. |
| 7,728,290 | B2 * | 6/2010 | Makarov ...................... 250/297 |
| 7,829,851 | B2 * | 11/2010 | McLuckey et al. ........... 250/292 |

(Continued)

FOREIGN PATENT DOCUMENTS

CA       2610051 A1 * 12/2006    ............. H01J 49/42

*Primary Examiner* — Jack Berman
(74) *Attorney, Agent, or Firm* — Thomas F. Cooney

(57) ABSTRACT

A method of obtaining and analyzing a mass spectrum of a sample comprising components is characterized by: setting values of a first energy level and a second energy level; chromatographically separating the components; ionizing a portion of the separated components to create precursor ions; introducing a first portion of the precursor ions into a collision or reaction cell and generating a first sub-population of ions corresponding to the first energy level; introducing a second portion of the precursor ions into the cell and generating a second sub-population of ions corresponding to the second energy level; transferring a mixture of the first and second sub-populations of ions into a mass analyzer; producing an analysis of the ions of the mixture; varying the value of at least one of the first and the second energy levels according to a pre-determined cyclical variation; repeating various above steps; and analyzing the time-variation of the analyses.

11 Claims, 13 Drawing Sheets

(56) References Cited

U.S. PATENT DOCUMENTS

| | | |
|---|---|---|
| 7,842,917 B2 * | 11/2010 | McLuckey et al. ........... 250/283 |
| 7,880,136 B2 * | 2/2011 | Makarov et al. .............. 250/282 |
| 8,410,424 B2 * | 4/2013 | Makarov et al. .............. 250/281 |
| 2006/0138320 A1 * | 6/2006 | Bateman ....................... 250/288 |
| 2006/0257963 A1 | 11/2006 | Cerda |
| 2008/0087809 A1 | 4/2008 | Russ et al. |
| 2011/0204218 A1 * | 8/2011 | Hager et al. .................. 250/282 |
| 2013/0228679 A1 * | 9/2013 | Makarov et al. .............. 250/282 |

* cited by examiner

US 8,748,809 B2

ACQUISITION AND ANALYSIS OF MIXED ION POPULATIONS IN A MASS SPECTROMETER

CROSS REFERENCE TO RELATED APPLICATIONS

This application is the United States National Stage Application, under 35 U.S.C. 371, of International Application PCT/US2010/029277 having an international filing date of Mar. 30, 2010, which claims the benefit of the filing date, under 35 U.S.C. 119(e), of U.S. Provisional Application 61/168,714, filed on Apr. 13, 2009.

TECHNICAL FIELD

This invention relates to mass spectrometry and in particular to methods for acquiring and analyzing ion populations comprising mixtures of precursor and fragment or reaction product ions.

BACKGROUND ART

In general, a mass spectrometer comprises an ion source for generating ions from molecules to be analyzed, and ion optics for guiding the ions to a mass analyzer. A tandem mass spectrometer further comprises a second mass analyzer. In tandem mass spectrometry, structural elucidation of ionized molecules is performed by collecting a mass spectrum, then using a first mass analyzer to select a desired precursor ion or ions from the mass spectrum, causing fragmentation of the selected precursor ions, and then performing mass analysis of the fragment ions using a second mass analyzer. Generally, a mass analyzer with accurate mass capability is preferable for the second mass analyzer. It is often desirable to obtain a mass spectrum of precursor ions also using the accurate-mass mass analyzer (accurate-mass MS), i.e. pass a sample of precursor ions to the accurate-mass MS without fragmentation. The method can be extended to provide one or more further stages of fragmentation (i.e. fragmentation of fragment ions and so on). This is typically referred to as $MS^n$, with the superscript n denoting the number of generations of ions. Thus $MS^2$ corresponds to tandem mass spectrometry.

To properly interpret the molecular and compositional information potentially available from a tandem mass spectrometry experiment, it is desirable to be able generate fragments of various sizes, to match each fragment to the particular precursor ion from which it was produced, and to measure fragment masses with high mass accuracy (parts-per-million, ppm) and high resolution (i.e., a mass resolution of one part in $10^5$ or better). Generation of fragments of various sizes may be accomplished by the $MS^n$ methods noted above or by performing separate fragmentation procedures (of similar precursors) at different levels of experimentally supplied energy. Matching between fragments and precursors is conventionally performed by isolating each precursor in turn for fragmentation and separately mass analyzing the fragments generated from each precursor. High resolution is generally obtained through the use of pulsed accurate-mass MS apparatuses, such as TOF analyzers, FT ICR analyzers and electrostatic trap (EST) analyzers such as the Orbitrap mass analyzer, an electrostatic trap analyzer.

Most of the accurate-mass MS apparatuses listed above have a short injection cycle followed by relatively long mass analysis stage, especially when operated at high resolution. These time requirements may be multiplied several-fold if separate mass analysis scans are required for each of several sets of fragments, each such set generated from a different precursor. Frequently, the analytes of interest are chemically complex molecules such as peptides or proteins derived from biological samples, requiring multiple fragmentations and associated analyses for unambiguous identification or characterization. Unfortunately, the analyte resolving power of modern chromatography techniques, such as high-performance liquid chromatography (HPLC) is sufficiently good that the entirety of the elution profile of an individual such analyte may last only a few seconds, from start to finish, thereby severely constraining the time available for the desired detailed analysis of precursor ions and fragment or product ions.

From the above discussion, it is evident that there is often a requirement for accurate and high resolution analysis of multiple sets of peptide fragments, from different precursors and produced at different energy levels, within tight time constraints. It is would therefore be desirable to be able to mass analyze all such precursors and fragments simultaneously, as a mixture, in a fashion that allows precursor-fragment correlation and that preserves mass resolution and accuracy. The present invention addresses such a need.

DISCLOSURE OF INVENTION

The present teachings envision using a multiple fill Higher Collision Energy Dissociation (HCD) cell (or a curved quadrupole trap, known as a C-trap cell) functionality of an accurate-mass mass analyzer system to avoid performing a separate full scan MS event and substitutes it with scan event which detects all ions originating from high and low collision energy fills simultaneously. This simultaneous analysis technique allows execution of all ion $MS^2$ experiments significantly faster than when discrete spectra are acquired at specified collision energy.

The proposed sequence starts from a full scan multiple fill mass spectrum of ions generated or acquired with both high and low energies (for instance, collision energies), which, in some embodiments, comprises HCD MS/MS on all ions coming into an accurate-mass MS instrument or which, in some embodiments, may comprise a conventional Collision Induced Dissociation (CID) cell. For those embodiments employing HCD fragmentation, the fragmentation is carried out with two or more ion fills at specified normalized collision energy (energies). To assure the presence of molecular ions in the spectrum, the first such fill needs to be done at the lowest relative collision energy, 0% normalized energy. The omission of one conventional full scan from the experimental sequence, in accordance with the invention, decreases the experimental cycle time significantly. The parent product ion-pairs can be later correlated, as they would have identical elution profiles.

In addition, if ion populations of high and low energy fills are modulated in every other scan or even less frequently (the frequency can be set manually based on the complexity of the mixture and the width of the LC peak), then the relative abundance change of the parent ions from adjacent scans (where at least one scan comprises a 0% normalized energy ion fill in order to preserve molecular ions) can be used as a confirmation that of parent-product identifications.

In case of multiple precursors which produce the same neutral loss (NL), the spectra as generated above would contain multiple pairs of molecular ions and their product ions resulting from NL. They would also mix with the fragment ions since the same neutral loss can be attributed to more than one of the precursors. To distinguish molecular ion-NL pairs from fragment ion-NL pairs, one can correlate the change in intensities in the fragments as well as parent ions. The elution profiles will be identical between fragments and their parents.

Accordingly, in a first aspect, there is provided a method of obtaining and analyzing a chromatography/mass spectrometry spectrum of a sample comprising at least two components, characterized by: a) setting a current value (that is, a currently-employed value) of a first energy level and a current value of a second energy level; b) separating the components of the sample using a chromatographic column; c) ionizing a portion of the separated components so as create precursor ions; d) introducing a first portion of the precursor ions into a collision or reaction cell so as to generate a first sub-population of ions corresponding to the first energy level; e) introducing a second portion of the precursor ions into the same or a different collision or reaction cell so as to generate a second sub-population of ions corresponding to the second energy level; f) transferring a mixture of the first sub-population of ions and the second sub-population of ions into a mass analyzer; g) producing a mass-to-charge analysis of the ions of the mixture of the first and second sub-populations of ions using the mass analyzer; h) expelling the first and second sub-populations of ions from the mass analyzer; i) varying the current value of at least one of the first and the second energy levels according to a pre-determined cyclical variation of energy; j) repeating steps c) through g); and j) producing an analysis of a time-variation of the mass-to-charge analysis, which may be used to match precursor and fragment ions.

In a second aspect, there is provided a method of obtaining and analyzing a chromatography/mass spectrometry spectrum of a sample comprising at least two components, characterized by: a) setting a current value of a first proportion of ions and a current value of a second proportion of ions; b) separating the components of the sample using a chromatographic column; c) ionizing a portion of the separated components so as create precursor ions; d) introducing a first portion of the precursor ions into a collision or reaction cell so as to generate a first sub-population of ions corresponding to a first energy level and to the first proportion; e) introducing a second portion of the precursor ions into the same or a different collision or reaction cell so as to generate a second sub-population of ions corresponding to a second energy level and to the second proportion; f) transferring a mixture of the first sub-population of ions and the second sub-population of ions into a mass analyzer; g) producing a mass-to-charge analysis of the ions of the mixture of the first and second sub-populations of ions using the mass analyzer; h) expelling the first and second sub-populations of ions from the mass analyzer; i) varying the current value of at least one of the first and the second proportions according to a pre-determined cyclical variation of the proportions; j) repeating steps c) through g); and k) producing an analysis of a time-variation of the mass-to-charge analysis, which may be used to match precursor and fragment ions.

In a third aspect, there is provided a method of obtaining and analyzing a chromatography/mass spectrometry spectrum of a sample comprising at least two components, characterized by: a) ionizing a portion of the separated components so as create precursor ions; b) introducing a first portion of the precursor ions into a collision or reaction cell so as to generate a first sub-population of ions corresponding to a first fragmentation method; c) introducing a second portion of the precursor ions into the same or a different collision or reaction cell so as to generate a second sub-population of ions corresponding to a second fragmentation method; d) transferring a mixture of the first sub-population of ions and the second sub-population of ions into a mass analyzer; e) producing a mass-to-charge analysis of the ions of the mixture of the first and second sub-populations of ions using the mass analyzer; f) expelling the first and second sub-populations of ions from the mass analyzer; g) repeating steps a) through e); and h) matching precursor ions to fragment or product ions based on a time-variation of the mass-to-charge analysis.

BRIEF DESCRIPTION OF DRAWINGS

The above noted and various other aspects of the present invention will become apparent from the following description which is given by way of example only and with reference to the accompanying drawings, not drawn to scale, in which.

MODES FOR CARRYING OUT THE INVENTION

This disclosure describes methods for acquisition and analysis of mixed ion populations in a mass spectrometer. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described.

To more particularly describe the features of the present invention, please refer to FIGS. 1A through 7B in conjunction with the discussion below.

Figure 1A:
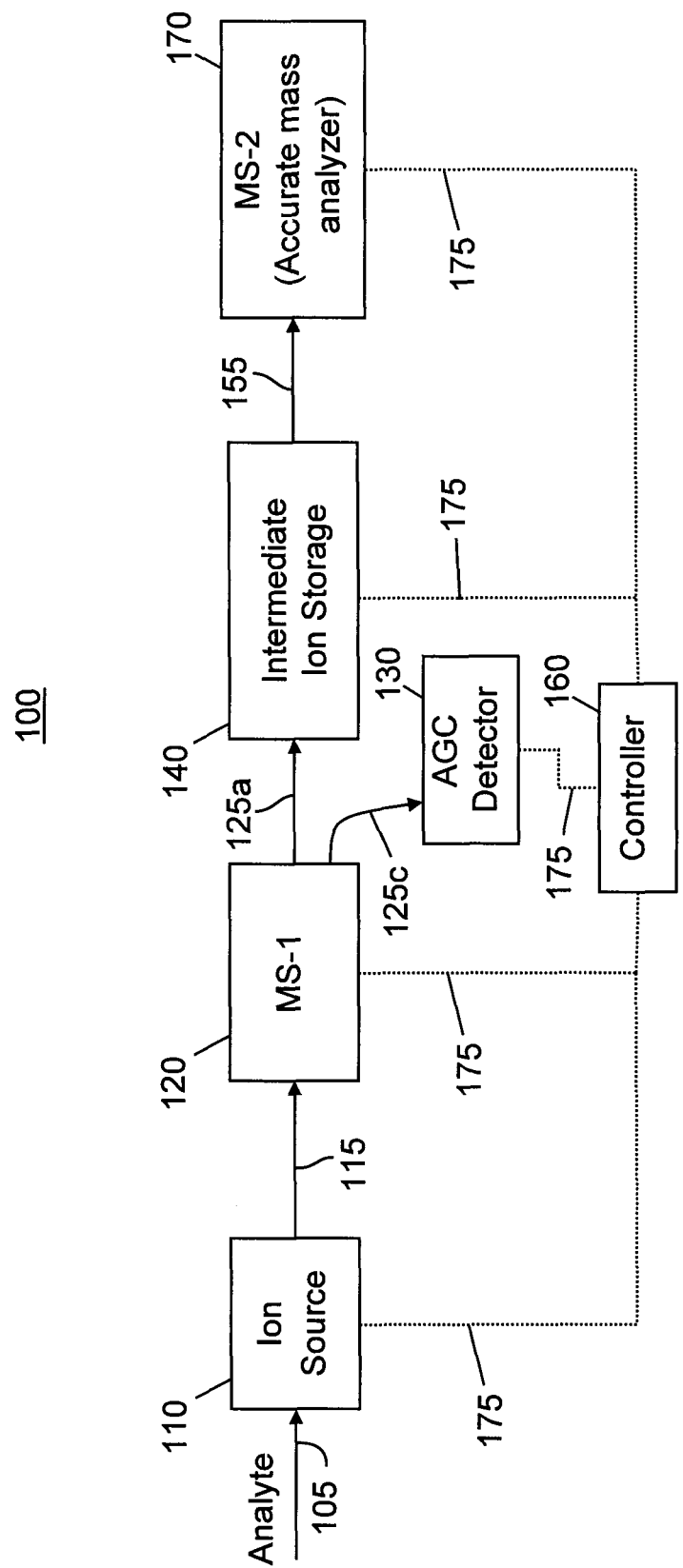
FIG. 1A is a schematic illustration of a first example of a generalized mass spectrometer system on which the invention according to some of its aspects may be practiced.

A first example of a generalized mass spectrometer system 100 on which the invention according to some of its aspects may be practiced is shown in FIG. 1A. Analyte material 105 is provided to a pulsed or continuous ion source 110 so as to generate ions 115. The ions are admitted to a first mass analyzer (MS-1) 120 that has mass analysis and mass selection functionality and in which, optionally, fragmentation may be performed. For instance, the first mass analyzer MS-1 may comprise an ion trap. Ion source 110 could be a MALDI source, an electrospray source or any other type of ion source. In addition, multiple ion sources may be used. Also, the mass analyzer MS-1 120 may be preceded by any number of other stages of mass analysis, and/or ion manipulation.

It is to be noted that, in the system of FIG. 1A as well as in other systems illustrated in subsequent drawings, ions are transferred from one component to the next via ion optics (e.g. RF multipoles) which, in some cases, are not specifically illustrated. Moreover, the drawings do not show the electrodes of the various parts—that are used to guide and/or trap ions within those parts.

An automatic gain control (AGC) detector 130 may be provided in the mass spectrometer system 100 (see FIG. 1A, for instance) to quantitatively measure or sample an ion flux or number of ions for purposes of controlling the number of ions in a subsequent ion population. Any of the known AGC methods may be used to determine the optimum ionization time for fills of the downstream intermediate ion storage 140 or the accurate-mass mass analyzer MS-2 170. Accordingly, a proportion of ions exiting MS-1 may be diverted along path 125c to AGC detector 130. Otherwise, ions are transferred from MS-1 along path 125a to the intermediate ion storage 140.

Automatic Gain Control (AGC) is the common name for utilization of information about an incoming ion stream to regulate the amount of ions admitted to a mass analyzer. This information may also be used to select mass ranges, based on spectral information. In this application, AGC is interpreted in a most general way as a method of determining an optimum fill time based on sampling a set of ions. Therefore, it includes not only methods based on information from a pre-scan or previous scan, but includes other methods of measuring numbers of ions such as a current sensing grid that intercepts (preferably uniformly) an ion beam; sensing induced currents; sensing scattered ions, for example on apertures; sensing secondary electrons; and using a previous analytical scan taken by the first mass analyzer 120. The Automatic Gain Control technique is described in further detail in U.S. Pat. No. 5,107,109 and U.S. Pat. No. 6,987,261. Different variants of measuring the initial ion abundance have been described, including using the total ion current in the previous spectra (U.S. Pat. No. 5,559,325), using a short pre-scan in which ions are transmitted through the trap towards the detector (WO 03/019614) and measuring a part of the ions stored in storage multipole prior to FT-ICR (U.S. Pat. No. 6,555,814).

Still with reference to the system 100 shown in FIG. 1A, selected ions are transferred from the first mass analyzer 120 along path 125a into the intermediate ion store 140 where they are captured and trapped. The intermediate ion store 140 may comprise, for instance, an ion trap device. Ions released from the intermediate ion store 140 are transferred along path 155 to an accurate-mass mass analyzer (MS-2) 170. The accurate-MS may receive, for analysis, either unfragmented precursor ions, a set of ions formed by fragmentation of a single selected precursor ion, or a mixture of a plurality of sets of ions, each such set formed by fragmentation of a different respective precursor ion. With reference to the systems illustrated herein, ions produced using the optimum ionization time may be fragmented in either the first mass analyzer 120 or a separate reaction cell, for example, by collision-induced dissociation. The accurate-mass MS has sufficiently high m/z resolution to resolve most or all species in such mixed ion populations. Examples of suitable accurate-mass mass analyzers are ion cyclotron resonance mass spectrometers and electrostatic trap mass spectrometers, such as the Orbitrap mass analyzer.

A controller 160, which may comprise a general purpose computer or, perhaps, a specialized electronic logic device, is electronically coupled to other components along electronic control lines 175. The electronic control lines 175 may send control signals from the controller 160 to the mass spectrometers, intermediate ion storage device, ion source, the various ion optics, etc. in order to control the coordinated operation of these components. For instance, the controller may send signals to set potentials on the electrodes of the various parts at the various appropriate times. The electronic control lines 175 may also transmit signals from one or more of the components of the system 100 back to the controller 160. For instance, the controller 160 may receive signals from the AGC detector 130 and from the accurate-mass MS 170, such signals relating to number of ions detected.

Figure 1B:
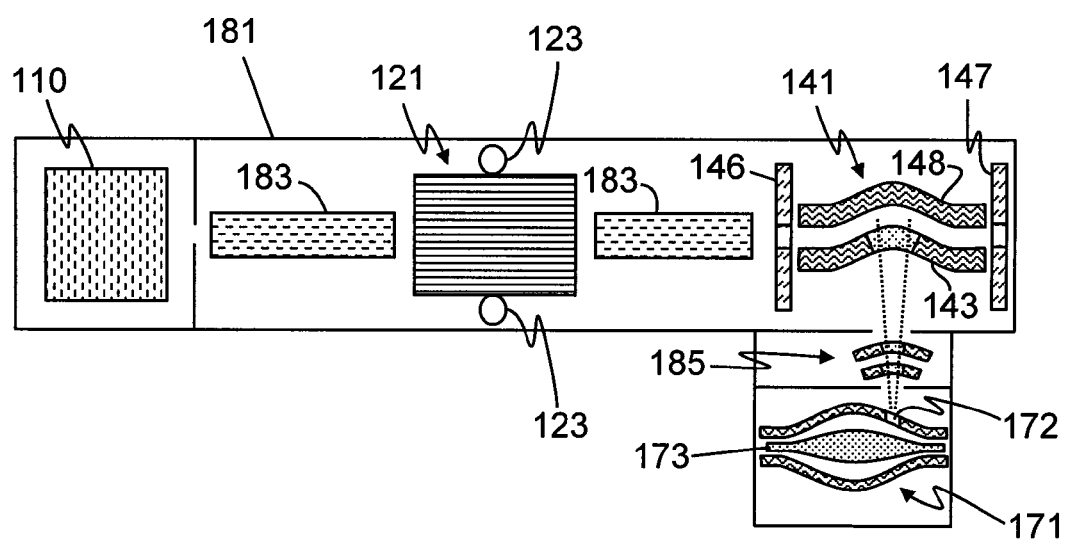
FIG. 1B is a schematic illustration of a particular mass spectrometer system on which the invention according to some of its aspects may be practiced, the system including an electrostatic trap mass analyzer.

An example of a mass spectrometer system 190 comprising an electrostatic trap mass analyzer such as an Orbitrap mass analyzer 171 is shown in FIG. 1B. In the illustrated system, the intermediate ion store comprises a curved quadrupole trap 141 (also known as a "C-trap") with a slot 144 in the inner electrode 143. Prior to ion injection, ions may be squeezed along the axis of the curved quadrupole trap 141 by raising voltages on end electrodes 146 and 147. For ion injection into the Orbitrap mass analyzer 171, the RF voltage on the curved quadrupole trap 141 is switched off, as is well known. Pulses are applied to electrodes 143 and 148 and to an electrode of curved ion optics 185 so that the transverse electric field accelerates ions into the curved ion optics 185. The converging ion beam that results enters the Orbitrap mass analyzer 171 through injection slot 172. The ion beam is squeezed towards the axis by an increasing voltage on a central electrode 173. Due to temporal and spatial focusing at the injection slot 172, ions start coherent axial oscillations. These oscillations produce image currents that are amplified and processed. Ions are transferred between components by ion optical assemblies 183. Further details of the electrostatic trap apparatus 171 are described in International Application Publication WO 02/078046, U.S. Pat. No. 5,886,346, U.S. Pat. No. 6,872,938. The entire apparatus is enclosed in a housing 181 which is evacuated in operation of the system.

In the system 190 shown in FIG. 1B, the mass analyzer MS-1 is represented as multipole ion trap 121 having detectors 123. A separate AGC detector (not shown) may also be included. AGC may also be employed using the detectors 123. Fragmentation or ion reaction may be performed in either the multipole ion trap 121 or the curved quadrupole trap 141 or both. For instance, the multipole ion trap 121 may be used as a conventional CID cell whereas the curved quadrupole trap 141 may be used as an HCD cell.

Figure 2A:
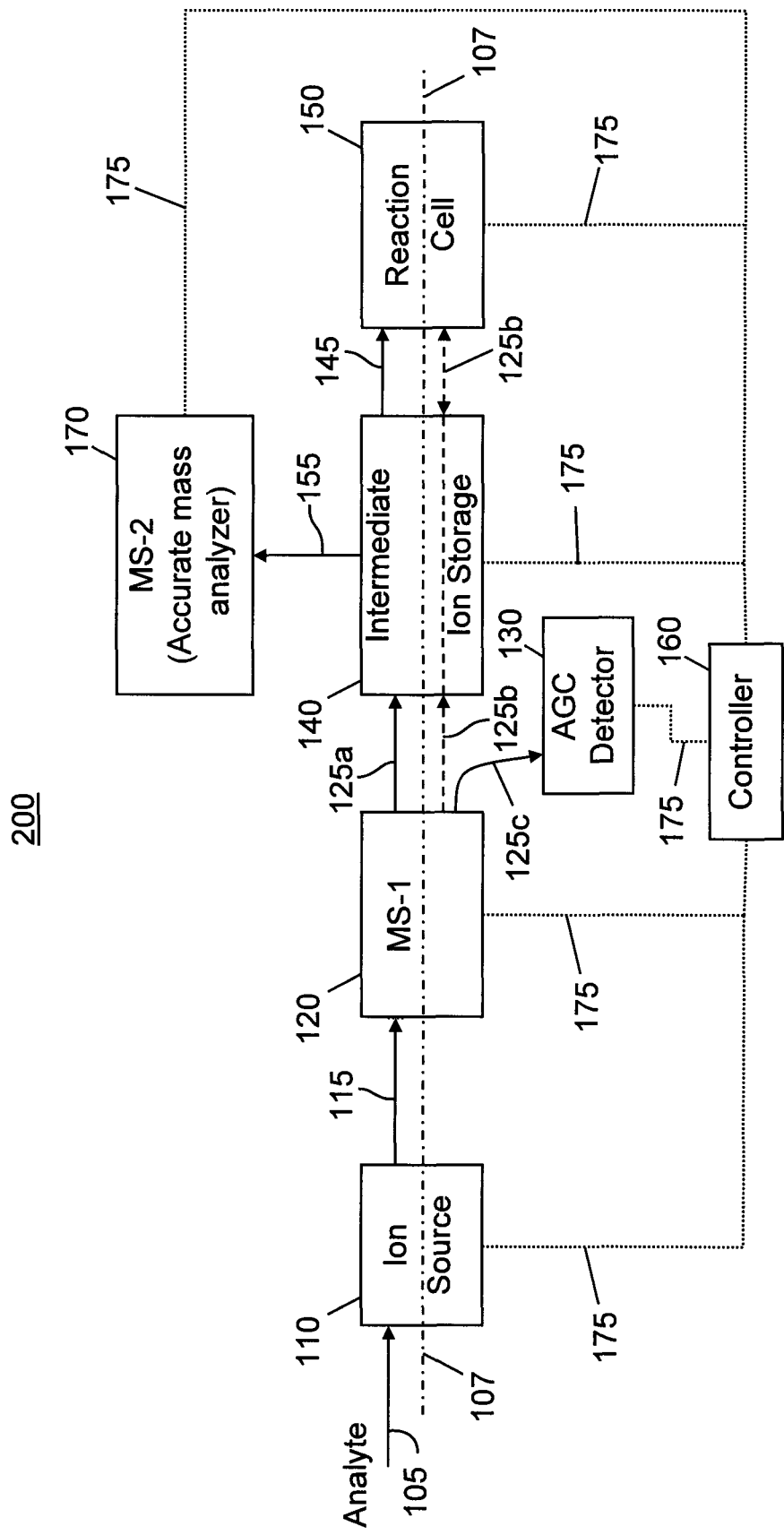
FIG. 2A is a schematic illustration of a second example of a generalized mass spectrometer system on which the invention according to some of its aspects may be practiced.

A second example of a generalized mass spectrometer system 200 on which the invention according to some of its aspects may be practiced is shown in FIG. 2A. The system 200 shown in FIG. 2A comprises all of the components as described with reference to the mass spectrometer system 100 (FIG. 1A), with similar reference numbers thus being used as in FIG. 1A. With reference to FIG. 2A, however, it is to be noted that, although most components of the mass spectrometer system 200 are positioned on the longitudinal "axis" 107 (shown as a dot-dash line), the accurate-mass mass analyzer MS-2 is positioned off of this axis. Further, a reaction cell for fragmentation of ions is disposed along axis 107 at the side of the intermediate ion storage device opposite to MS-1. Although the curve 107 is shown as a straight line and referred to as an "axis", it should be noted that, in practice, at least a portion of this curve may not, in fact, be a straight line.

The system 200 shown in FIG. 2A (and also the system 300 shown in FIG. 3A) provides for two types of ion pathways between the first mass analyzer MS-1 120 and the accurate-mass mass analyzer MS-2 170, corresponding to two respective modes of operation. In a first mode of operation, selected ions are delivered along pathway 125a from MS-1 to the intermediate ion storage device 140 where they are trapped. Once a suitable time delay has passed, the controller 160 transports the ions to the reaction cell 150. In a second, alternative, mode of operation, the intermediate ion storage device 140 is used merely as an ion guide ("transmission mode") such that ions are transferred along pathway 125b (which may, in fact be coincident with path 125a but which is shown offset from that pathway, for clarity) from MS-1 to the reaction cell 150. The intermediate ion store 140 may be filled with gas, thereby reducing the energy of the ions through collisional cooling as they pass through the intermediate ion store and enter the reaction cell 150.

Precursor ions may be fragmented in the reaction cell 150. Ion fragmentation may be effected by any suitable fragmentation technique, such as collision-induced dissociation (CID), electron transfer dissociation (ETD), electron capture dissociation (ECD) or infrared multi-photon dissociation (IRMPD). The resulting fragment ions (if any) or precursor ions (if any) are then transferred, in the opposite direction, back along path 125b from the reaction cell to the intermediate ion storage device 140. After storage in the intermediate ion storage device 140 for an appropriate time, these fragment ions are transferred to the accurate-mass MS 170 for analysis along pathway 155. Multiple fills of the accurate-mass MS 170 may be formed using different respective processing techniques (for instance, high energy versus low energy fragmentation) in the reaction cell 150. The flexibility provided by these various operation options provides the capability of performing both precursor ion as well as fragment ion analyses using the accurate-mass MS.

Figure 2B:
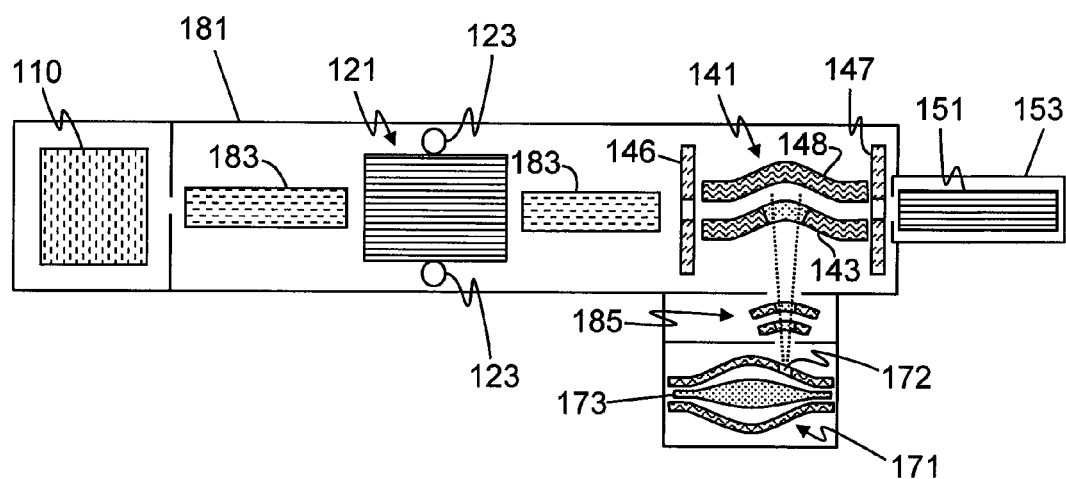
FIG. 2B is a schematic illustration of another particular mass spectrometer system on which the invention according to some of its aspects may be practiced, the system including an electrostatic trap mass analyzer.

A second example of a mass spectrometer system comprising an electrostatic trap mass analyzer such as an Orbitrap mass analyzer is shown in FIG. 2B. The system 290 shown in FIG. 2B is generally similar to the system 190 shown in FIG. 1B, except that the system 290 further comprises reaction cell 151, which may comprise a collision cell (such as an octopole) that is enclosed in a gas tight shroud 153 and that is aligned to the curved quadrupole trap 141, as shown in FIG. 2B. The reaction cell 153, when used as a collision cell, may be supplied with an RF voltage of which the DC offset can be varied. A collision gas line (not shown) may be attached and the cell is pressurized with nitrogen (or any) gas.

Higher energy collisions (HCD) may take place in the system 290 as follows: Ions of a determined number, either mass selected or not, are transferred from the multipole ion trap 121 (MS-1) to the curved quadrupole trap 141. The curved quadrupole trap is held at ground potential. For HCD, ions are emitted from the curved quadrupole trap 141 to the octopole of the reaction cell 151 by setting a voltage on a trap lens. Ions collide with the gas in the reaction cell 151 at an experimentally variable energy which may be represented as a relative energy depending on the ion mass, charge, and also the nature of the collision gas (i.e., a normalized collision energy). Thereafter, the product ions are transferred from the reaction cell back to the curved quadrupole trap by raising the potential of the octopole. A short time delay (for instance 30 ms) is used to ensure that all of the ions are transferred. In the final step, ions are ejected from the curved quadrupole trap 141 into the Orbitrap analyzer 171 as described previously. HCD can be used to generate a series of ions which are typical of higher-energy fragmentation processes. The net outcome of such a procedure is the observation of some diagnostic ions which are not normally seen during conventional CID fragmentation, for instance, iminium ions which are characteristic of phosphotyrosine.

Multiple fill experiments may be performed in the system 290 as follows: Ions from the multipole ion trap 121 are injected multiple times into the curved quadrupole trap 141. Ions from the multipole ion trap 121 can be of the same type or they can be different, viz., mass isolated, collision activated, higher order collision activated, etc. Multiple energy HCD experiments are performed by passing ions from the multipole ion trap 121, following each individual fill in the ion trap, into the reaction cell 151 at different collision energy offsets. The sum of fragment ions from all fills in the reaction cell are transferred to the curved quadrupole trap 141 where they are then ejected into the Orbitrap analyzer 171. Likewise, a population of ions can be built up in the curved quadrupole trap 141 through multiple fills from the multipole ion trap 121 and then sent to the reaction cell 151, or, alternatively, sent directly to the Orbitrap analyzer 171.

Each fill described above, may correspond to a different energy or even method of collisional activation of the precursor ion of choice. Each fill could correspond to an incremental change in activation or collision energy such that the final ion population corresponds to an entire activation/collision energy range. This method allows acquisition of a "collisional energy scan" in a single spectrum of the mass analyzer and maximizes sequence coverage. Also, additional fragmentation methods could be used for some fills, for example IR multi-photon dissociation, electron transfer dissociation, electron-capture dissociation, etc. The latter could be arranged within the first mass analyzer MS-1, the ion optics, or the curved quadropole trap or other intermediate ion store. Providing additional dimensions of structural information, these methods could be used in combination with multiple filling as a powerful tool for de-novo sequencing of peptides and proteins.

Figure 3A:
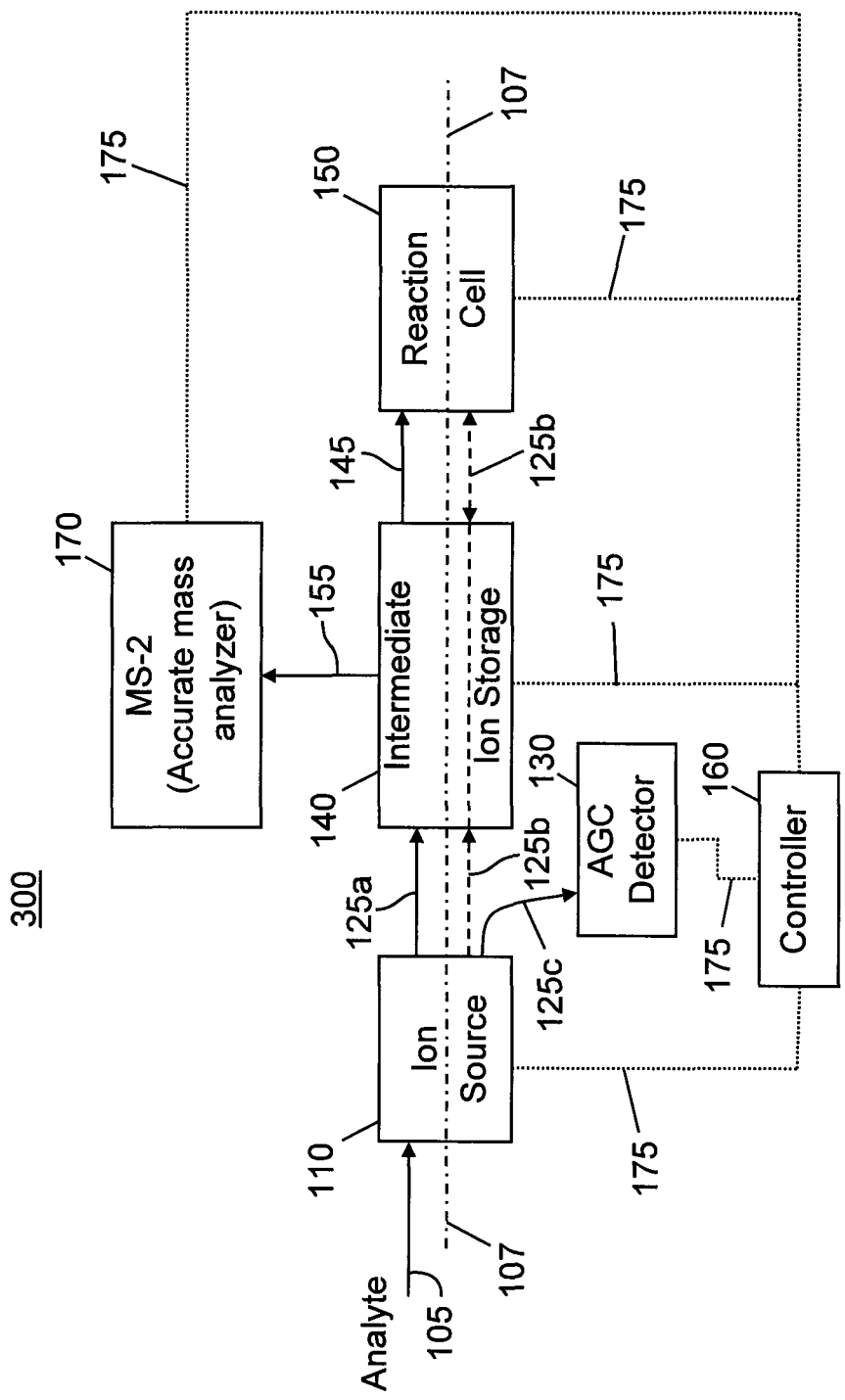
FIG. 3A is a schematic illustration of a third example of a generalized mass spectrometer system on which the invention according to some of its aspects may be practiced.
Figure 3B:
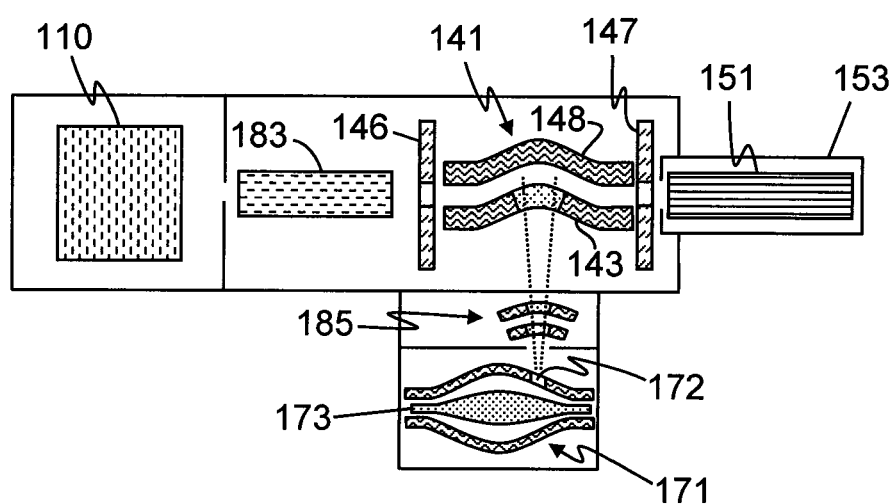
FIG. 3B is a schematic illustration of still another particular mass spectrometer system on which the invention according to some of its aspects may be practiced, the system including an electrostatic trap mass analyzer.

FIG. 3A illustrates a third example of a generalized mass spectrometer system 300 on which the invention according to some of its aspects may be practiced. The mass spectrometer system 300 is similar to the system 200 illustrated in FIG. 2A, except that the system 300 does not comprise a first mass spectrometer MS-1. Thus, in the system 300, the ion source 110 delivers, to either or both of the intermediate ion storage device 140 and the reaction cell 150, streams or pulses of ions which are not pre-selected or pre-isolated according to their m/z. A specific example of a system lacking a first mass spectrometer (MS-1) is shown as system 390 in FIG. 3B. Except for the absence of the multipole ion trap 121 (i.e., MS-1), the components of the system 390 are similar to those illustrated in FIG. 2B.

Figure 4:
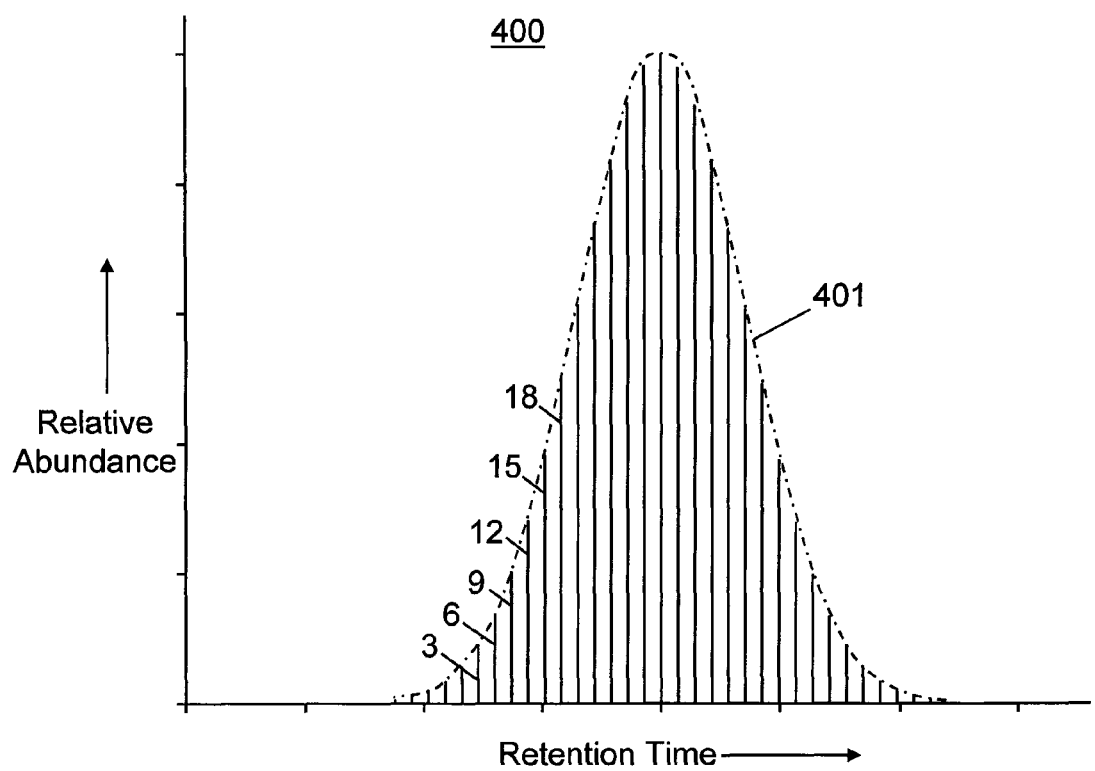
FIG. 4 is a schematic illustration of a profile of a measure of total precursor ion relative abundance as may be measured by multiple scans of a mass spectrometer during elution of an analyte in a chromatographic/mass spectrometric analysis apparatus.

Graph 400 in FIG. 4 is a schematic illustration of a profile of a measure of total precursor ion population during elution of an analyte in a chromatographic/mass spectrometric analysis apparatus (such as a GC-MS or LC-MS apparatus) having an accurate-mass MS analyzer instrument. Accordingly, the dashed curve (or peak) 401 is a hypothetical continuous curve representing the total number of ions produced, at any instant in time, by an ion source of a mass spectrometer as an eluting analyte is delivered to the ion source. The number of ions produced by the ion source, as represented by curve 401, is assumed to be proportional to the mass of eluting analyte, at any instant in time.

Although ions are essentially continuously delivered to the accurate-mass MS analyzer from the ion source, the accurate-mass MS only analyzes discrete samples of the ion flux, each such analysis requiring a finite time interval to conduct the analysis. For convenience of discussion, each discrete analysis performed by the mass analyzer is referred to as a "scan" or a "mass scan" herein. However, it is to be kept in mind, despite this terminology, that many accurate-mass mass analyzers generate information on ionic mass or mass-to-charge composition without actually sequentially scanning, per se, the ionic masses. Vertical lines in FIG. 4 represent hypothetical discrete samples of the precursor ions produced by the ion source, a selected six of which are labeled as samples 3, 6, 9, 12, 15 and 18. Each of these vertical lines may be considered as a sample of the elution curve 401.

The gaps (not to scale) between the vertical lines in FIG. 4 and other drawings of this document generally represent periods of time required to obtain a scan measurement. During the time that each scan is being performed, the accurate-mass MS generally cannot admit additional ions. During such time, incoming ions (i.e., from an ion source) may be temporarily stored, for instance within first mass analyzer (MS-1) 120 of FIG. 1A or FIG. 2A, within multipole ion trap 121 of FIG. 1B or FIG. 2B, within intermediate ion storage 140 of FIG. 3A, or within the curved quadrupole trap 141 of FIG. 3B. Once the accurate-mass MS has completed a scan, the ions contained therein are ejected or neutralized and a portion or all of the stored ions are then admitted into the accurate-mass MS and a new scan is begun.

For purposes of discussion, each of the solid vertical lines, e.g., samples 3, 6, 9, 12, 15 and 18, may be considered to represent the hypothetical relative abundance of precursor ions that would be measured in a scan of a sample of ions as produced by the ion source, that is, a sample of ions that are not fragmented or otherwise reacted. As envisioned, however, scans will generally be performed on either precursor ions, fragment ions, mixtures of precursors together with fragments, or mixtures of fragments produced at high energy and at low energy. Therefore, depending on the type of reaction or fragmentation employed, the nature of the sample and various experimental conditions, the number of ions measured in any individual scan may be either less than, equal to or greater than that indicated by the height of the solid vertical lines.

Figure 5A:
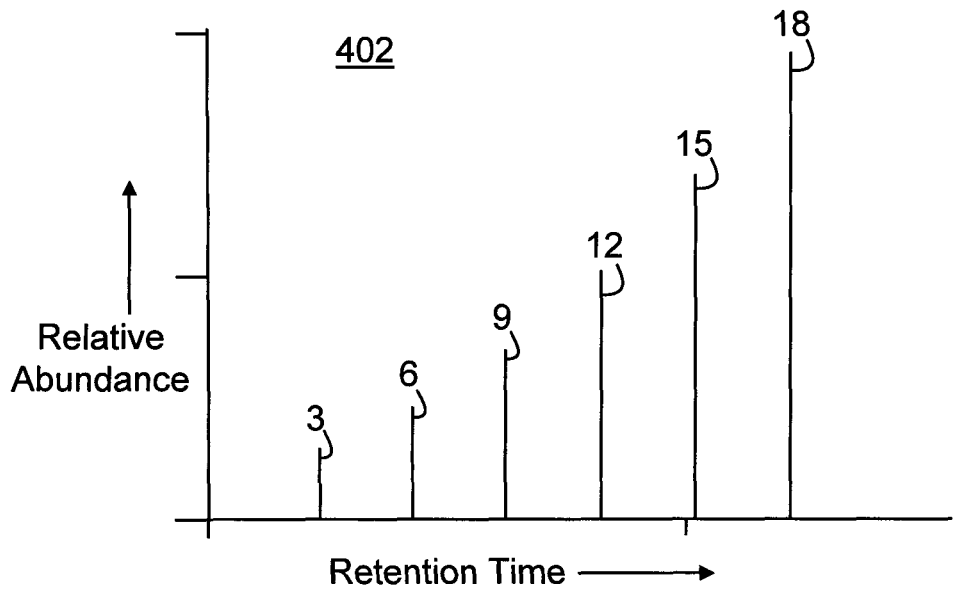
FIG. 5A is an expanded view of a portion of the profile of total precursor ion abundance shown in FIG. 4.
Figure 5B:
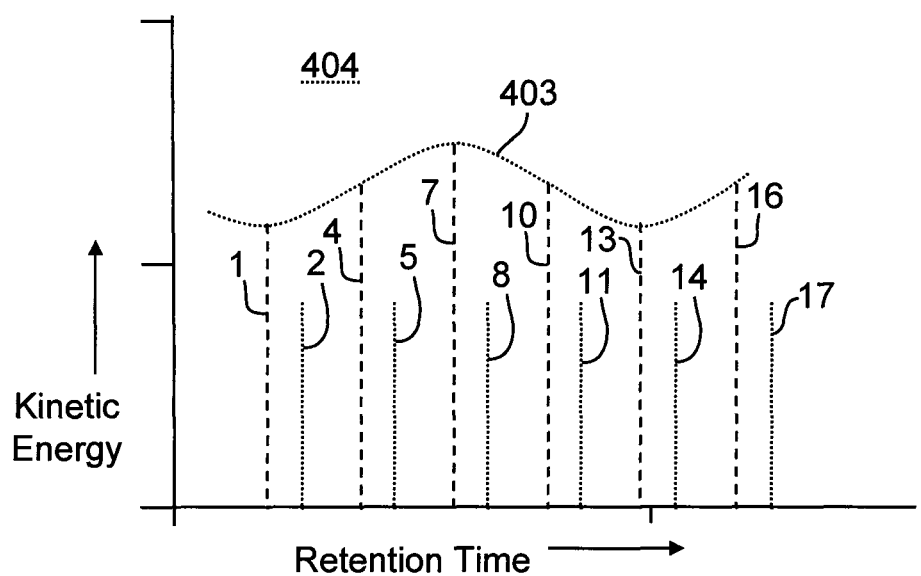
FIG. 5B is a schematic graphical illustration of generation, in accordance with some embodiments of the invention, of a set of mixed ionic populations in a collision or reaction cell of a mass spectrometer instrument, wherein the supplied energy of a high-energy sub-population of each mixed population of ions is varied between populations in a periodic fashion.

Graph 402, shown in FIG. 5A, is an expanded version of a portion of the graph 400 of FIG. 4, showing the particular hypothetical samples 3, 6, 9, 12, 15 and 18. Graph 404, shown in FIG. 5B, is an illustration of individual sub-populations corresponding to the samples, wherein, in accordance with various embodiments of the invention, each sub-population corresponds to ions supplied from a collision or reaction cell. Dashed lines represent sub-populations generated in a collision or reaction cell under relatively high-energy conditions (for instance, high collision energy regimes); dotted lines represent sub-populations generated under relatively low-energy conditions. The sub-populations may be generated separately in a reaction or collision cell and then a pre-determined number of such sub-populations (for instance, pairs of the sub-populations) are admitted to and scanned together in an accurate-mass MS, as described previously herein. For instance, as illustrated in FIGS. 5A-5B, precursor sample 3 approximately corresponds to sub-populations 1 and 2, precursor sample 6 approximately corresponds to sub-populations 4 and 5, precursor sample 9 approximately corresponds to sub-populations 7 and 8, precursor sample 12 approximately corresponds to sub-populations 10 and 11, precursor sample 15 approximately corresponds to sub-populations 13 and 14, and precursor sample 18 approximately corresponds to sub-populations 16 and 17. In this example, sub-populations 1 and 2 are admitted into and scanned together in the mass analyzer as a mixed ion population. Likewise each successive pair of sub-populations (for instance, sub-populations 4 and 5, sub-populations 7 and 8, etc.) is mixed in the mass analyzer and scanned together as a mixed ion population.

In this context of this discussion, the term "high-energy sub-population" is used in a relative sense to refer to ions generated within a reaction cell or collision cell at relatively higher energy (relative to the low energy scans) so as to promote fragmentation or reaction of precursor ions in the reaction cell. The term "low-energy sub-population" is used similarly in a relative sense, except that at least one such low energy sub-population should correspond to a situation in which few or no precursor ions are fragmented or reacted. The reaction cell may comprise the reaction cell 150 of FIG. 2A and FIG. 3A or the reaction cell 151 of FIG. 2B and FIG. 3B. Alternatively, in some apparatus, the first mass analyzer MS-1 120 (FIGS. 1A and 2A), the multipole ion trap 123 (FIGS. 1B and 2B) or the curved quadrupole 141 (FIG. 1B) may be employed as a reaction cell, as is known in the art. Separate respective reaction cells may be employed for high-energy and low-energy scans.

FIG. 5B represents one possible form of modulation of the scans, in accordance with some embodiments of the invention. In the example shown in FIG. 5B, each scan of the accurate-mass MS corresponds to a mixture between one high-energy and one low-energy sub-population wherein: (a) the energy of each low-energy sub-population is sufficiently low such that few or no precursor ions are fragmented or reacted and wherein (b) the energy of the high-energy sub-populations is cyclically varied. Line 403 in FIG. 5B outlines an envelope of this variation or modulation, which, in this example, is applied only to the high-energy scans. It is to be noted that the high- and low-energy scans need not alternate, one-for-one, as shown in FIG. 5B and that various alternative modulation patterns, perhaps encompassing different numbers of scans per cycle, could be employed.

Figure 5C:
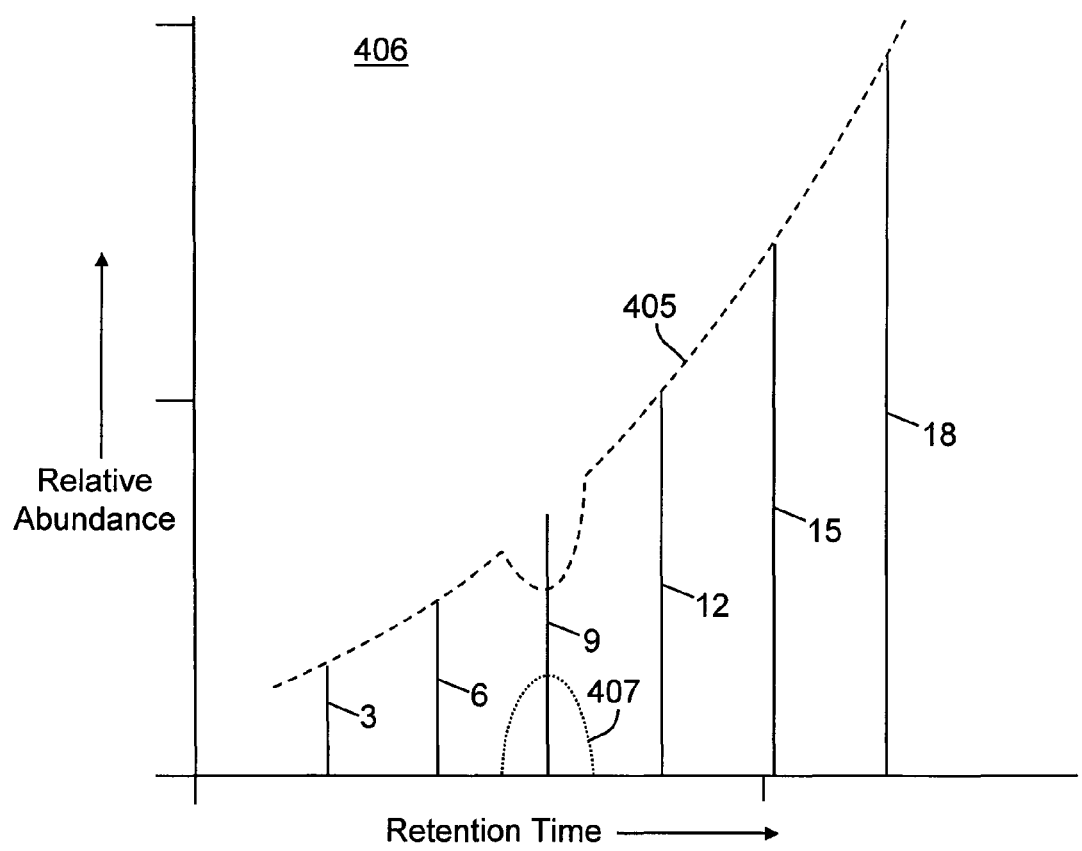
FIG. 5C is a schematic graphical illustration of expected variation of some proportions of precursor and fragment ions between mass spectrometer scans in response to the kinetic energy variation illustrated in FIG. 5B.

Because changing the energy of collision or reaction in a collision cell generally causes a change in the extent and mechanism of fragmentation or reaction, the relative proportions of precursor ions and fragment or product ions will generally vary between scans and this variation will exhibit a correlation to the imposed scan modulation. For instance, FIG. 5C shows, in schematic fashion, an example of antithetic variation (or negatively correlated behavior) between a measured population of fragment ions (curve 407) and a measured population of precursor ions (curve 405) that would occur as the high energy fragmentation or reaction exceeds a particular threshold energy. In this example, the maximum in the fragment or product ion population and the associated minimum in the precursor ion population correlate with the maximum in the modulation curve 403 (FIG. 5B) that occurs near the time associated with sample 9 (FIG. 5A). Since the modulation curve 403 is periodic, similar antithetic variations between precursors and fragments or products would be observed at other portions of the elution profile (graph 400, FIG. 4). Since intermediate fragments or products may, upon further fragmentation or reaction, give rise to secondary fragments or products, similar relationships will be observed between the measured amounts of such intermediate and secondary ionic species. The existence and extent of these various relationships may be determined by application of signal processing techniques to the set of collected data.

Figure 6A:
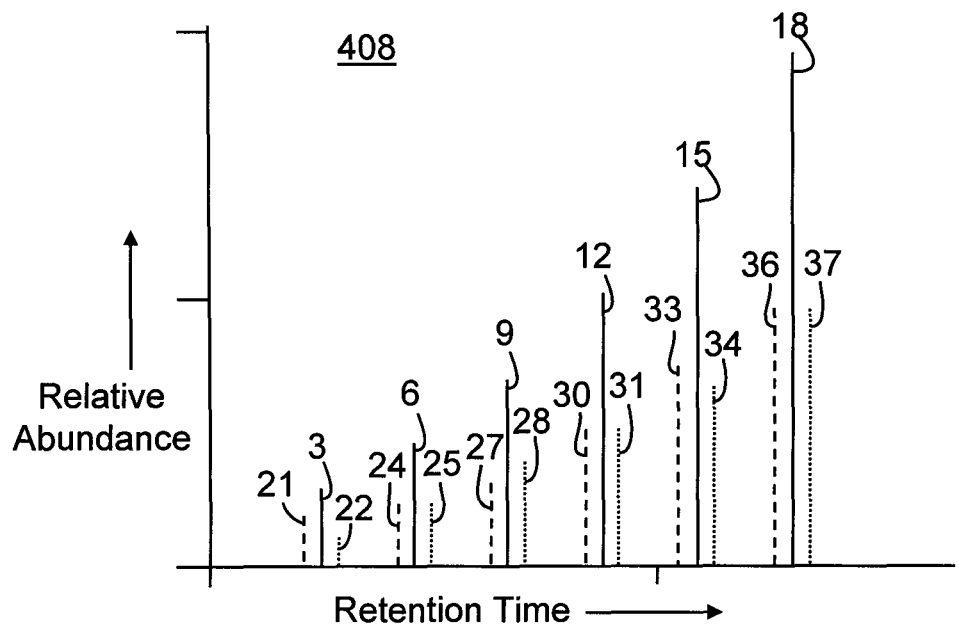
FIG. 6A is a schematic graphical illustration of generation, in accordance with some embodiments of the invention, of a set of mixed ionic populations in a collision or reaction cell of a mass spectrometer instrument, wherein the relative proportions of a high-energy sub-population and a low-energy sub-population are varied between populations in a periodic fashion.
Figure 6B:
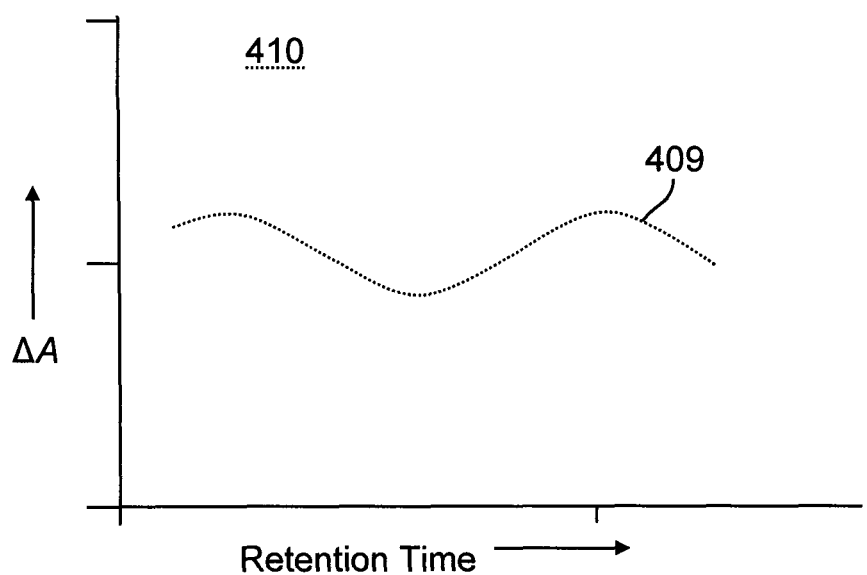
FIG. 6B is a schematic graphical illustration of expected variation, between mass spectrometer scans, of the difference in ionic abundance between high-energy and low-energy sub-populations of ions in response to the variation illustrated in FIG. 6A.

FIG. 6A is a schematic graphical illustration of analysis of a set of mixed ionic populations in a collision or reaction cell of a mass spectrometer instrument by modulation of the number of ions admitted into the collision or reaction cell for generating each sub-population. For instance, with reference to FIG. 2A, ion optics or an ion gate (not shown) between the intermediate ion storage 140 and the reaction cell 150 may be configured so as to admit a certain number of ions into the reaction cell 150 for high-energy collision dissociation or reaction and to admit a certain different number of ions into the reaction cell 150 for low-energy collision dissociation or reaction. The required times for admission of the appropriate numbers of ions may be determined using any of the methods of AGC, described previously. Further, the ion gate may be opened for varying periods of time such that the relative proportions of ions admitted for high-energy and low-energy collision dissociation or other reaction are periodically varied. One example of such variation is illustrated in FIG. 6A, in which the heights of the vertical dashed and dotted lines respectively represent the relative proportions of precursor ions admitted into the collision or reaction cell for high- and low-energy fragmentation or reaction. Precursor sub-populations 21 and 22 approximately correspond to sample 3, precursor sub-populations 24 and 25 approximately correspond to sample 6, precursor sub-populations 27 and 28 approximately correspond to sample 9, precursor sub-populations 30 and 31 approximately correspond to sample 12, precursor sub-populations 33 and 34 approximately correspond to sample 15 and precursor sub-populations 36 and 37 approximately correspond to sample 18.

The differences in the relative proportions, ΔA, between each pair of precursor sub-populations may be varied in a periodic fashion as shown by modulation envelope 409 of graph 410 (FIG. 6B) as well as by the relative heights of pairs of lines in FIG. 6A. Thus, for instance, comparing precursor sub-populations 21 and 22, it is seen that more than half of the precursor ions approximately corresponding to sample 3 are admitted to a collision or reaction cell for high energy fragmentation. Conversely, comparing, for instance, precursor sub-populations 27 and 28, it is seen that fewer than half of the precursor ions approximately corresponding to sample 9 are admitted for high energy fragmentation or reaction. In this example, the ion fragments or product ions derived from each pair of precursor sub-populations are admitted into the accurate-mass MS together and scanned together. The accurate mass scans are thus performed on mixed ion populations in which the ratio of precursor ions to fragment or product ions will vary in an out-of-phase fashion to the modulation curve 409. In this way, precursor ions can be distinguished from the product or fragment ions.

Figure 7:
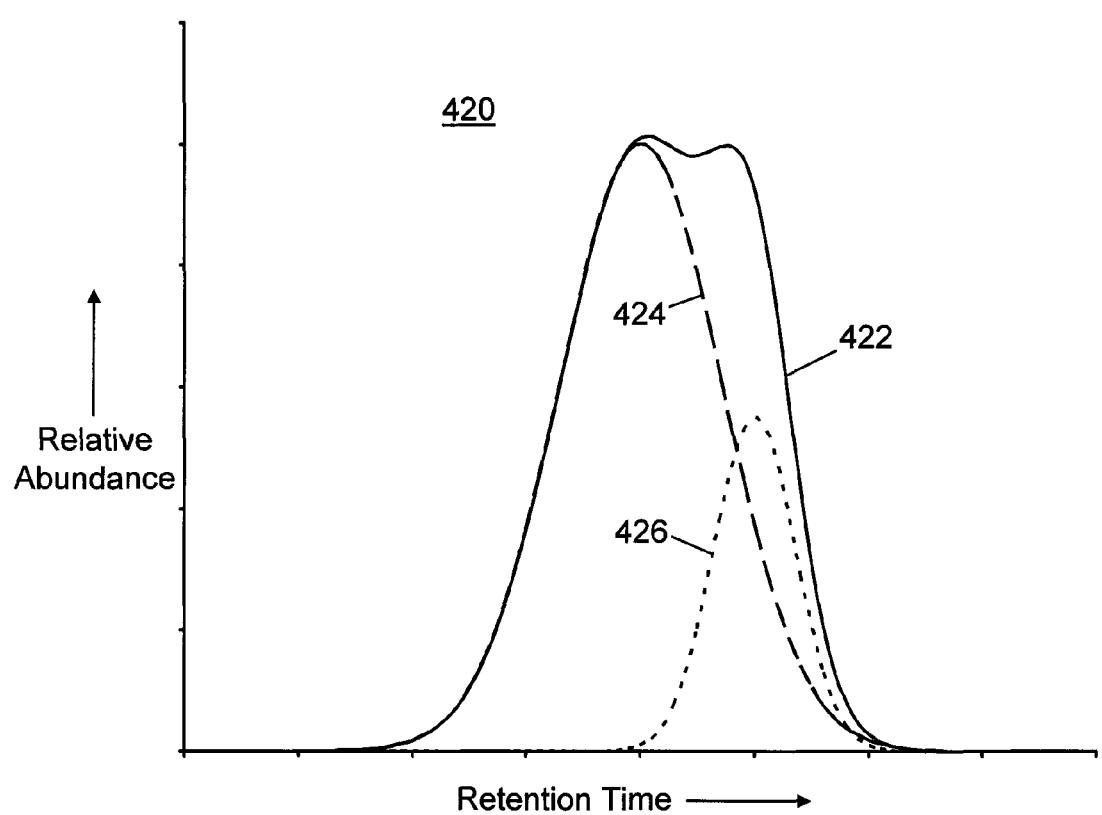
FIG. 7 is a schematic illustration of a profile of a measure of ion abundance as may be measured by a mass spectrometer during co-elution of analytes in a chromatographic/mass spectrometric analysis apparatus or system.

FIG. 7 is a schematic illustration of a profile of a measure of ion abundance as may be measured by a mass spectrometer during co-elution of analytes in a chromatographic/mass spectrometric analysis apparatus. In graph 420 of FIG. 7, curve 424 represents a hypothetical elution profile of a first analyte and curve 426 represents a hypothetical elution profile of a second analyte that partially co-elutes with the first analyte. Curve 422 is the summation of the two elution curves 424 and 426 and represents the elution profile as would be observed, for instance, in a total ion chromatogram, in a selected ion chromatogram or, generally, in any chromatographic experimental result obtained with an apparatus or system that does not have mass analysis capability.

In the context of the present invention, the elution profile 422 (FIG. 7) may be obtained using a mass spectrometer system comprising an accurate-mass MS apparatus as illustrated in any of FIGS. 1A-3B using the methods described in this disclosure. When the measurement is obtained in such a fashion, then, as described previously, the elution curve 422 will be sampled using a finite set of mass spectrometer scans, wherein each scan is performed on a mixed ionic population and wherein a property of at least one of the populations is modulated across or between scans. Alternatively, sequences of scans may comprise full scans of precursor or fragmented ions which alternate with scans of fragments produced in an HCD cell, with scans of fragments produced by low-energy fragmentation, or with scans of mixed ion populations containing both precursor and fragment ions. Various other combinations of precursors and fragments are possible. As noted previously, these methods can enable identification of precursor and fragment or product ions as well as correlation of precursor ions to their associated fragment or product ions. In particular, when partially co-eluting analytes (as in FIG. 7) give rise to different populations of fragments or reaction products, the analysis can be extended so as to match these fragment or reaction product populations to a particular one of the co-eluting analytes (or to eliminate one or more of the analytes as candidate matches) based on the elution profile, as a function of time. With reference to FIG. 7, for instance, the elution profile, as a function of time, for analyte-specific populations of precursors, fragments or reaction products would be expected to follow the pattern of either curve 424 or curve 426. If masses from alternate scans show the same elution profile at identical retention time they may be correlated with one another.

Figure 8A:
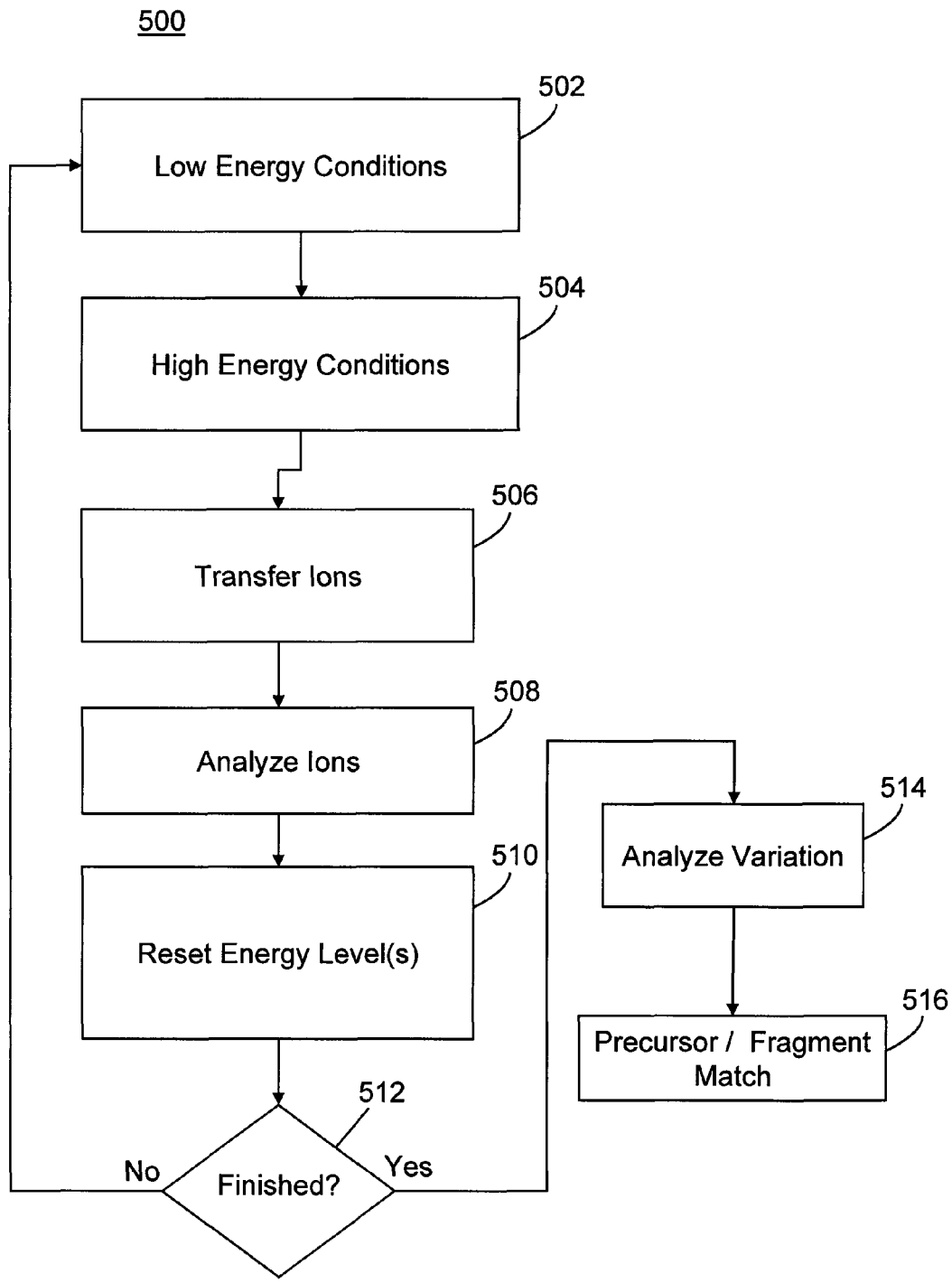
FIG. 8A is a flowchart of a first exemplary method for acquisition and analysis of mixed ion populations in a mass spectrometer in accordance with the invention.

In accordance with the above discussions, FIG. 8A is a flowchart of a first exemplary method for acquisition and analysis of mixed ion populations in a mass spectrometer in accordance with the invention. In the first step, Step 502, of the method 500 outlined in FIG. 8A, ions are generated or collected in a collision or reaction cell under low energy conditions. In the next step, Step 504, fragment or product ions are generated or collected in a collision or reaction cell under high energy conditions. The collision or reaction cell employed in Step 504 may be either the same cell as or a different cell from the one employed in step 502. In Step 506, the generated or acquired ions are transferred from the collision or reaction cell (or cells) to an accurate-mass mass analyzer and, in Step 508, the generated or acquired ions are analyzed by the accurate-mass MS. In the next step, Step 510 of the method 500, the high energy level for a subsequent high-energy fragmentation or reaction step is set to a new value in accordance with a pre-determined cyclical variation. If, in decision Step 512, the experiment has not completed, then execution of the method proceeds back to Step 502, in which ions corresponding to another sample are generated or acquired. Otherwise, execution of the method proceeds to Step 514 in which the variation of measured ion abundances versus time is analyzed to identify correlations or anti-correlations in the measured abundances. Finally, in Step 516, the results of the analysis are used to match precursor ions to fragment or product ions or to match precursor, fragment or product ions to a particular analyte.

Figure 8B:
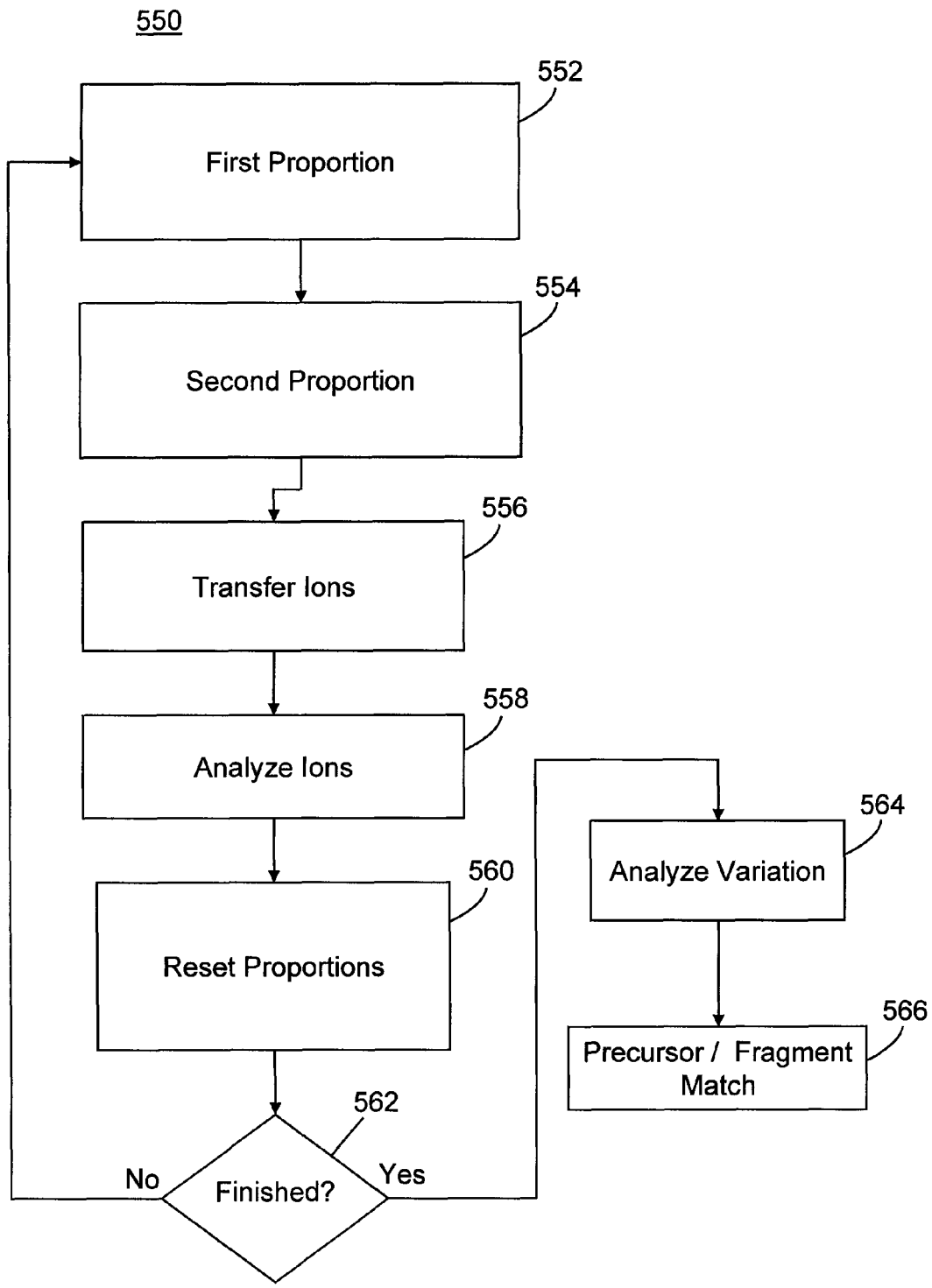
FIG. 8B is a flowchart of a second exemplary method for acquisition and analysis of mixed ion populations in a mass spectrometer in accordance with the invention.

FIG. 8B is a flowchart of a second exemplary method for acquisition and analysis of mixed ion populations in a mass spectrometer in accordance with the invention. In the first step, Step 552 of the method 550 outlined in FIG. 8B, ions are generated or collected in a collision or reaction cell under low energy conditions according to a first proportion. Next, in Step 554 ions are generated or collected in a collision or reaction cell under high energy conditions according to a second proportion. The collision or reaction cell employed in Step 554 may be either the same cell as or a different cell from the one employed in step 552. In Step 556, the generated or acquired ions are transferred from the collision or reaction cell (or cells) to an accurate-mass MS and, in Step 508, the generated or acquired ions are analyzed by the accurate-mass MS. In the next step, Step 560 of the method 550, the first or second proportions are reset to new values for subsequent high-energy and low-energy fragmentation or reaction steps, wherein the first and second proportions are reset according to a predetermined cyclical variation. If, in decision Step 562, the experiment has not completed, then execution of the method proceeds back to Step 552, in which ions corresponding to another sample are generated or acquired. Otherwise, execution of the method proceeds to Step 564 in which the variation of measured ion abundances versus time is analyzed to identify correlations or anti-correlations in the measured abundances. Finally, in Step 516, the results of the analysis are used to match precursor ions to fragment or product ions or to match precursor, fragment or product ions to a particular analyte.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the spirit, scope and essence of the invention. Neither the description nor the terminology is intended to limit the scope of the invention. Any and all publications referenced in this document are incorporated by reference herein in their entirety.

What is claimed is:

1. A method of obtaining and analyzing a chromatography/mass spectrometry spectrum of a sample comprising at least two components, characterized by:
   a) setting a current value of a first energy level and a current value of a second energy level;
   b) separating the components of the sample using a chromatographic column;
   c) ionizing a portion of the separated components so as create precursor ions;
   d) introducing a first portion of the precursor ions into a collision or reaction cell so as to generate a first sub-population of ions corresponding to the first energy level;
   e) introducing a second portion of the precursor ions into the same or a different collision or reaction cell so as to generate a second sub-population of ions corresponding to the second energy level;
   f) transferring a mixture of the first sub-population of ions and the second sub-population of ions into a mass analyzer;
   g) producing a mass-to-charge analysis of the ions of the mixture of the first and second sub-populations of ions using the mass analyzer;
   h) expelling the first and second sub-populations of ions from the mass analyzer;
   i) varying the current value of at least one of the first and the second energy levels according to a pre-determined cyclical variation of energy;
   j) repeating steps c) through g); and
   k) producing an analysis of a time-variation of the mass-to-charge analysis.

2. The method of claim 1, wherein the mass analyzer is chosen from the group consisting of ion cyclotron resonance mass analyzers and electrostatic trap mass analyzers.

3. The method of claim 1, further characterized by:
   l) matching precursor ions to fragment or product ions based on the time-variation analysis.

4. The method of claim 1, further characterized by:
   l) matching precursor ions, fragment ions or product ions to an analyte based on the time-variation analysis.

5. A method of obtaining and analyzing a chromatography/mass spectrometry spectrum of a sample comprising at least two components, characterized by:
   a) setting a current value of a first proportion of ions and a current value of a second proportion of ions;
   b) separating the components of the sample using a chromatographic column;
   c) ionizing a portion of the separated components so as create precursor ions;
   d) introducing a first portion of the precursor ions into a collision or reaction cell so as to generate a first sub-population of ions corresponding to a first energy level and to the first proportion;
   e) introducing a second portion of the precursor ions into the same or a different collision or reaction cell so as to generate a second sub-population of ions corresponding to a second energy level and to the second proportion;
   f) transferring a mixture of the first sub-population of ions and the second sub-population of ions into a mass analyzer;
   g) producing a mass-to-charge analysis of the ions of the mixture of the first and second sub-populations of ions using the mass analyzer;
   h) expelling the first and second sub-populations of ions from the mass analyzer;
   i) varying the current value of at least one of the first and the second proportions according to a pre-determined cyclical variation of the proportions;
   j) repeating steps c) through g); and
   k) producing an analysis of a time-variation of the mass-to-charge analysis.

6. The method of claim 5, wherein the mass analyzer is chosen from the group consisting of ion cyclotron resonance mass analyzers and electrostatic trap mass analyzers.

7. The method of claim 5, further characterized by:
l) matching precursor ions to fragment or product ions based on the time-variation analysis.

8. The method of claim 5, further characterized by:
l) matching precursor ions, fragment ions or product ions to an analyte based on the time-variation analysis.

9. A method of obtaining and analyzing a chromatography/mass spectrometry spectrum of a sample comprising at least two components, characterized by:
a) ionizing a portion of the separated components so as create precursor ions;
b) introducing a first portion of the precursor ions into a collision or reaction cell so as to generate a first sub-population of ions corresponding to a first fragmentation method;
c) introducing a second portion of the precursor ions into the same or a different collision or reaction cell so as to generate a second sub-population of ions corresponding to a second fragmentation method;
d) transferring a mixture of the first sub-population of ions and the second sub-population of ions into a mass analyzer;
e) producing a mass-to-charge analysis of the ions of the mixture of the first and second sub-populations of ions using the mass analyzer;
f) expelling the first and second sub-populations of ions from the mass analyzer;
g) repeating steps a) through e); and
h) matching precursor ions to fragment or product ions based on a time-variation of the mass-to-charge analysis.

10. The method of claim 9, wherein the mass analyzer is chosen from the group consisting of ion cyclotron resonance mass analyzers and electrostatic trap mass analyzers.

11. The method of claim 9, further characterized by:
i) matching precursor ions, fragment ions or product ions to an analyte based on the time-variation of the mass-to-charge analysis.

* * * * *